(12) United States Patent
Serbousek

(10) Patent No.: US 7,615,052 B2
(45) Date of Patent: Nov. 10, 2009

(54) SURGICAL INSTRUMENT AND METHOD

(75) Inventor: Jon Serbousek, Memphis, TN (US)

(73) Assignee: Warsaw Orthopedic, Inc.

( * ) Notice: Subject to any disclaimer, the term of this patent is extended or adjusted under 35 U.S.C. 154(b) by 185 days.

(21) Appl. No.: 11/117,301

(22) Filed: Apr. 29, 2005

(65) Prior Publication Data
US 2006/0247648 A1 Nov. 2, 2006

(51) Int. Cl.
A61B 17/00 (2006.01)

(52) U.S. Cl. ................... 606/79; 623/17.11

(58) Field of Classification Search ............. 606/79, 606/105, 206–207; 623/16.11, 17.11–17.16
See application file for complete search history.

(56) References Cited

U.S. PATENT DOCUMENTS

| | | | | |
|---|---|---|---|---|
| 3,916,907 A | * | 11/1975 | Peterson | 606/90 |
| 4,898,161 A | | 2/1990 | Grundei | |
| 5,059,193 A | | 10/1991 | Kuslich | |
| 5,529,571 A | | 6/1996 | Daniel | |
| 5,685,826 A | | 11/1997 | Bonutti | |
| 5,690,606 A | | 11/1997 | Slotman | |
| 5,697,889 A | * | 12/1997 | Slotman et al. | 600/204 |
| 5,865,802 A | | 2/1999 | Yoon et al. | |
| 6,017,342 A | * | 1/2000 | Rinner | 606/57 |
| 6,261,296 B1 | | 7/2001 | Aebi et al. | |
| 6,551,316 B1 | * | 4/2003 | Rinner et al. | 606/57 |
| 6,558,392 B1 | | 5/2003 | Martini | |
| 6,676,665 B2 | * | 1/2004 | Foley et al. | 606/105 |
| 6,712,825 B2 | | 3/2004 | Aebi et al. | |
| 6,716,218 B2 | | 4/2004 | Holmes et al. | |
| 6,739,068 B1 | * | 5/2004 | Rinner | 33/783 |
| 6,761,723 B2 | * | 7/2004 | Buttermann et al. | 606/79 |
| 2001/0031969 A1 | | 10/2001 | Aebi et al. | |
| 2002/0026197 A1 | | 2/2002 | Foley et al. | |
| 2002/0077632 A1 | | 6/2002 | Tsou | |
| 2003/0220645 A1 | * | 11/2003 | Suddaby | 606/79 |
| 2003/0220650 A1 | | 11/2003 | Major et al. | |
| 2003/0225416 A1 | * | 12/2003 | Bonvallet et al. | 606/105 |
| 2004/0039397 A1 | | 2/2004 | Weber et al. | |
| 2004/0106927 A1 | | 6/2004 | Ruffner et al. | |
| 2004/0153064 A1 | | 8/2004 | Foley et al. | |
| 2005/0070898 A1 | * | 3/2005 | Jones | 606/53 |
| 2005/0182413 A1 | * | 8/2005 | Johnson et al. | 606/79 |

* cited by examiner

Primary Examiner—Eduardo C Robert
Assistant Examiner—Tara R George

(57) ABSTRACT

Embodiments of the invention include devices and methods for manipulating bone. Instruments of some of the embodiments are insertable into a vertebral body or between vertebral bodies to apply forces to the vertebral bodies to strengthen bone or prepare bone to be strengthened.

24 Claims, 12 Drawing Sheets

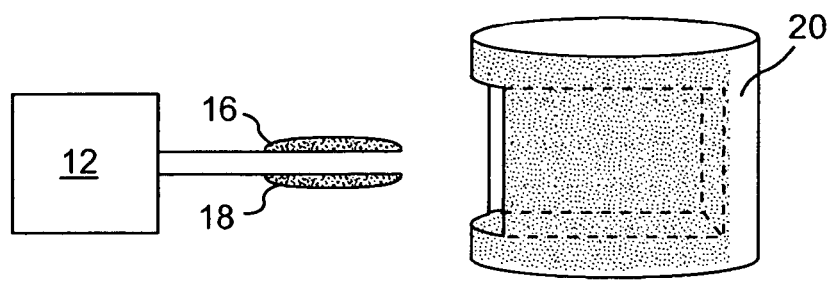
FIG. 2(e)
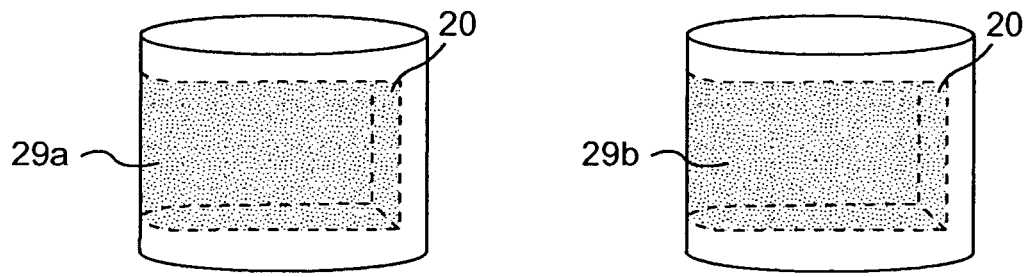
FIG. 2(f)(1)   FIG. 2(f)(2)

FIG. 4(e)  FIG. 4(f)

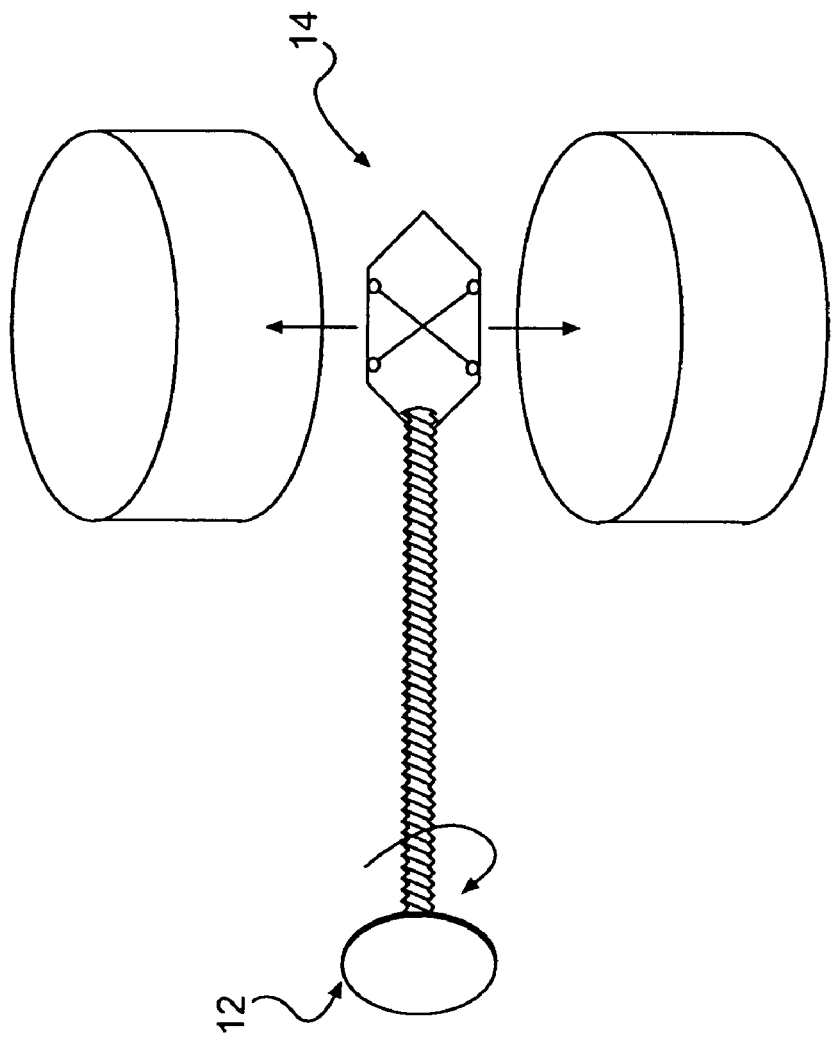

SURGICAL INSTRUMENT AND METHOD

BACKGROUND OF THE INVENTION

1. Field of the Invention

The invention relates to an apparatus and method for strengthening, reshaping and/or manipulating bone.

2. Description of the Related Art

Adjacent spinal vertebrae are separated by an intervertebral disc. Both the vertebrae and the disc can become damaged, requiring repair. Many techniques have been developed for repairing spinal structures including vertebroplasty, kyphoplasty, primary disc arthroplasty, revision disc arthroplasty, a window osteotomy accompanied bone grafting or mechanical insert fusion, pedicle screw fixation, and spinal fusion. These techniques may involve either the bonding of a material to a vertebra or vertebrae (spinal fusion, vertebroplasty, kyphoplasty, a window osteotomy accompanied by bone grafting or mechanical insert fusion) and/or the positioning of a mechanical element through or between vertebrae (pedicle screw fixation, primary disc arthroplasty, revision disc arthroplasty). The success of bonding may depend, in part, on the strength of the vertebral bone to which the added material becomes bonded. The success of mechanical-element insertion may depend, in part, on the strength of the vertebral body, because both the insertion process and the normal activity of the patient after surgery generate vertebral stress that is more easily withstood if the vertebrae are strengthened.

SUMMARY OF THE INVENTION

An embodiment of the present invention relates to an instrument for strengthening two spaced apart portions of bone. The instrument comprises first and second fixed shape, bone displacing and compressing elements that are sized and configured to be positionable within a space between the two spaced apart portions of bone. The first and second elements are movable to displace and compress the two spaced apart portions of bone, respectively. The instrument also comprises an actuator connected to the first and second elements and configured to actuate the first and second elements to displace and compress the two spaced apart portions of bone with sufficient force and for a sufficient amount of time to substantially strengthen the two spaced apart portions of bone.

Another embodiment of the present invention relates to a method of strengthening two spaced apart portions of bone. The method comprises inserting an instrument having two fixed shaped elements into a space between the two spaced apart portions of the bone, and applying a displacing and compressing force with each of the two fixed shape elements to one of the two spaced apart portions of bone with sufficient force and for a sufficient amount of time to substantially strengthen the two spaced apart portions of bone.

Still another embodiment of the present invention relates to an instrument for manipulating two spaced apart portions of bone. The instrument comprises first and second fixed shape means, positionable within a space between the two spaced apart portions of bone, for displacing and compressing the two spaced apart portions of bone, respectively, after being inserted into the space. The instrument also comprises means for actuating the first and second fixed shape means to displace and compress the two spaced apart portions of bone, respectively, after being inserted into the space, with sufficient force and for a sufficient amount of time to substantially manipulate the two spaced apart portions of bone.

Other features of the present invention will become more apparent upon consideration of the following detailed description of preferred embodiments taken in conjunction with the accompanying drawings.

BRIEF DESCRIPTION ON THE DRAWINGS

FIGS. 4(a) through 4(g) are schematic diagrams showing an intervertebral embodiment of the apparatus and vertebrae to which it is applied.

Figure 5:
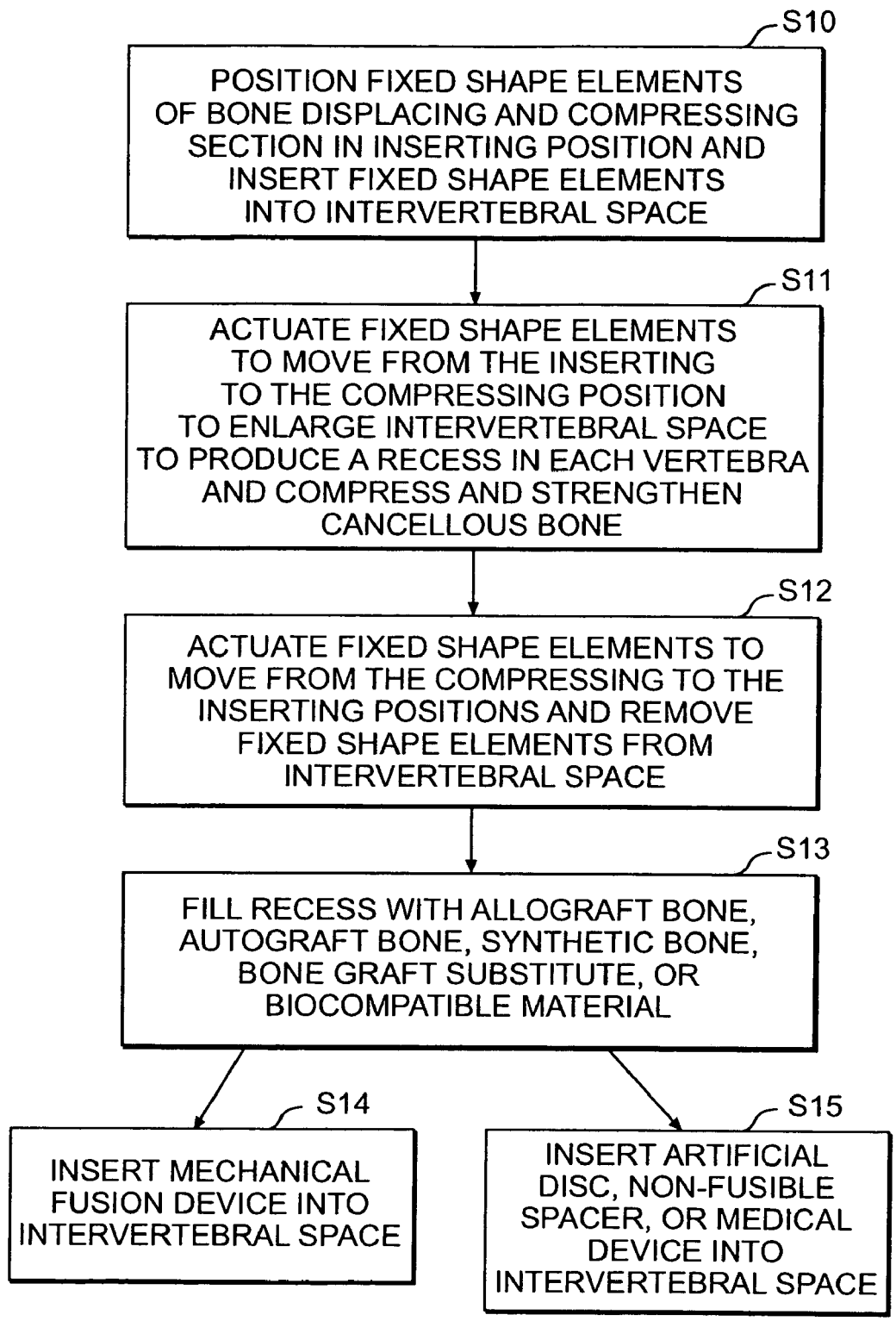

FIG. 5 shows a flow chart of an intervertebral method.

Figure 6:
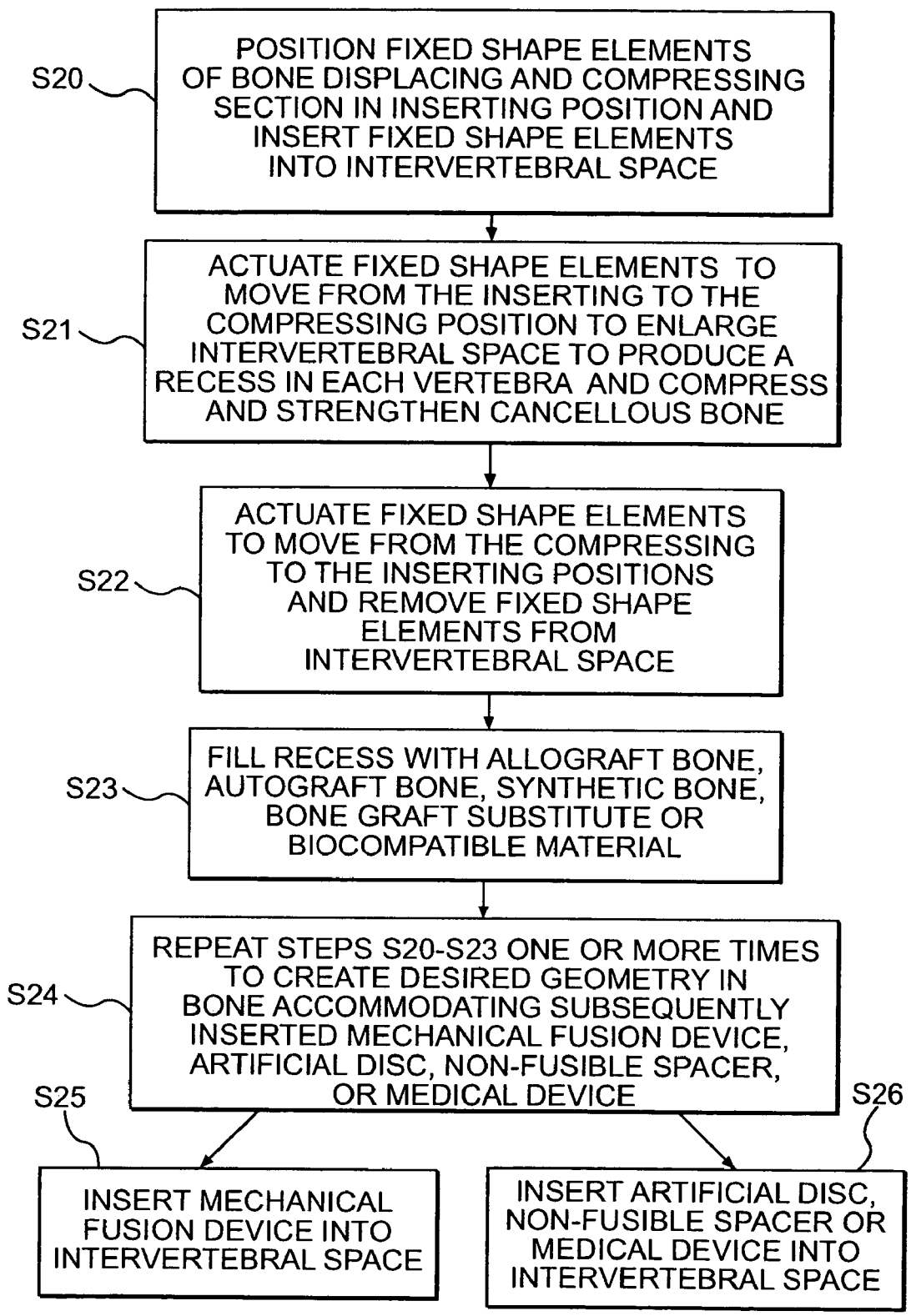

FIG. 6 shows a flow chart of an alternative embodiment of the intervertebral method.

Figure 7:
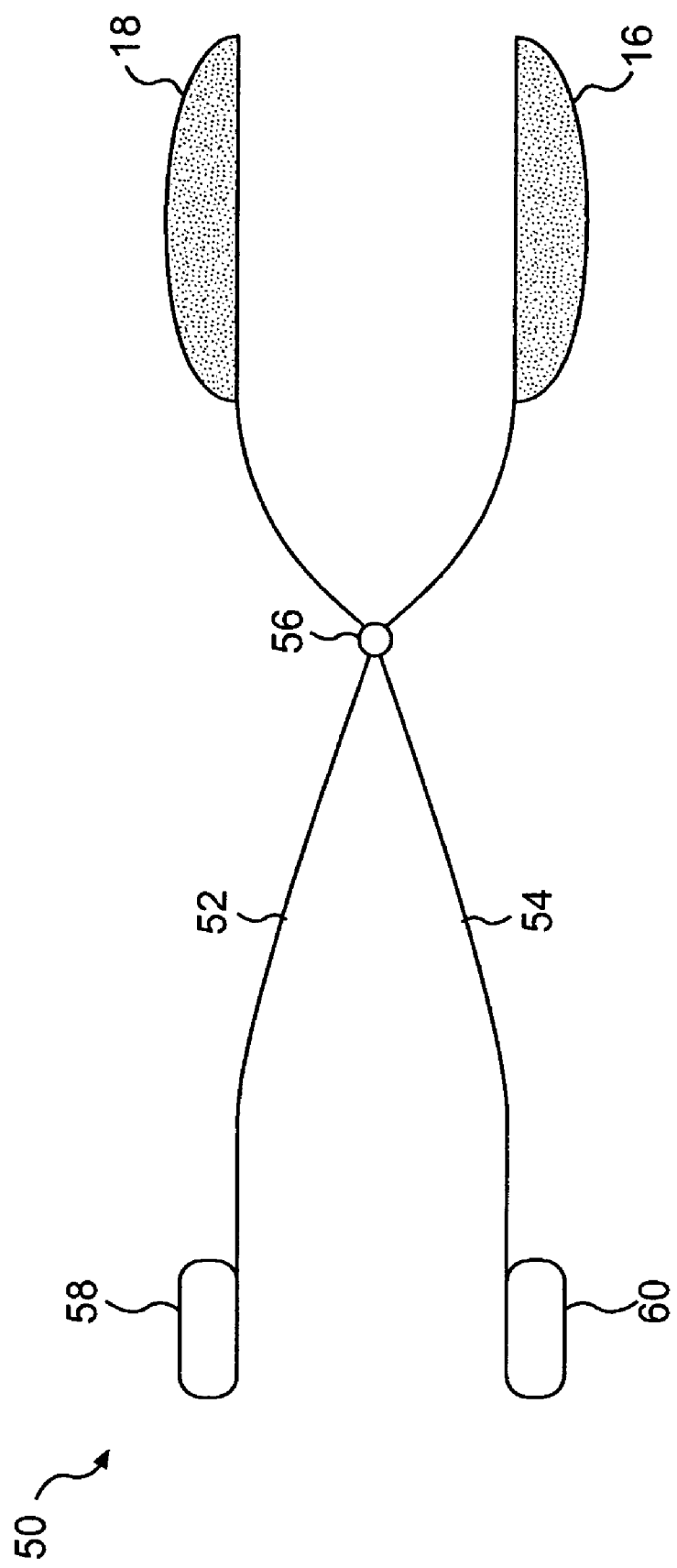

FIG. 7 shows a schematic diagram of one embodiment of a mechanical actuator.

Figure 8:
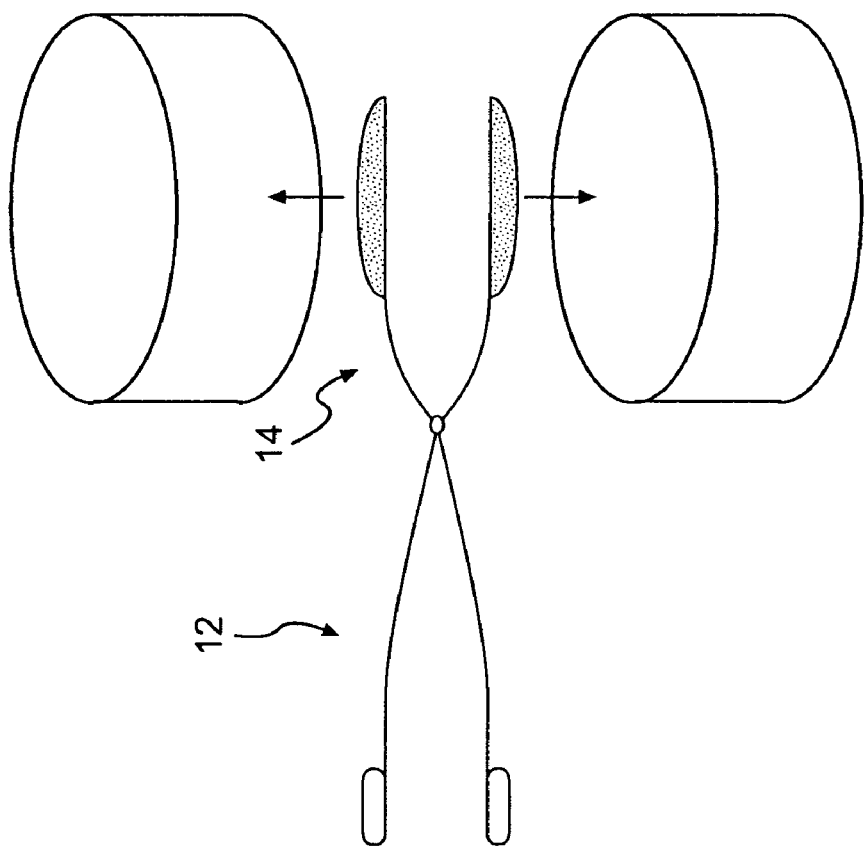
Figure 8:
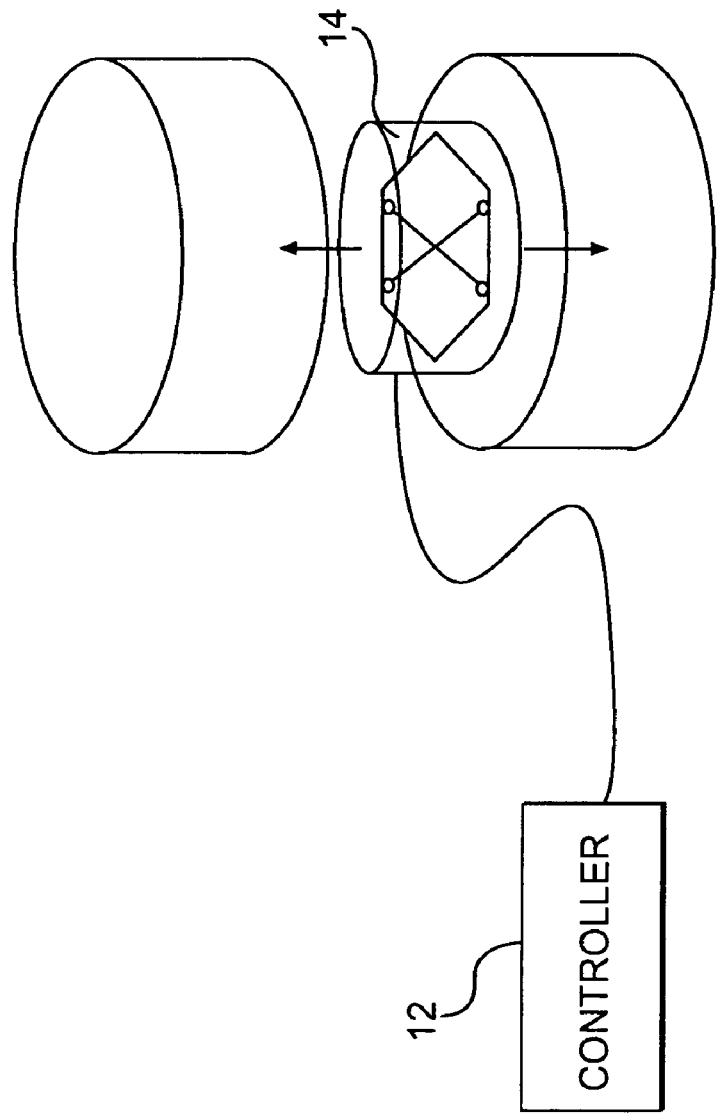

FIG. 8(a) shows a schematic diagram of the embodiment of the mechanical actuator shown in FIG. 7 whose displacing and compressing section is positioned between two spaced apart portions of bone.

FIGS. 8(b) and 8(c) show schematic diagrams of additional embodiments of a mechanical actuator and an electromechanical actuator, respectively, whose displacing and compressing sections are positioned between two spaced apart portions of bone.

DETAILED DESCRIPTION

Figure 1:
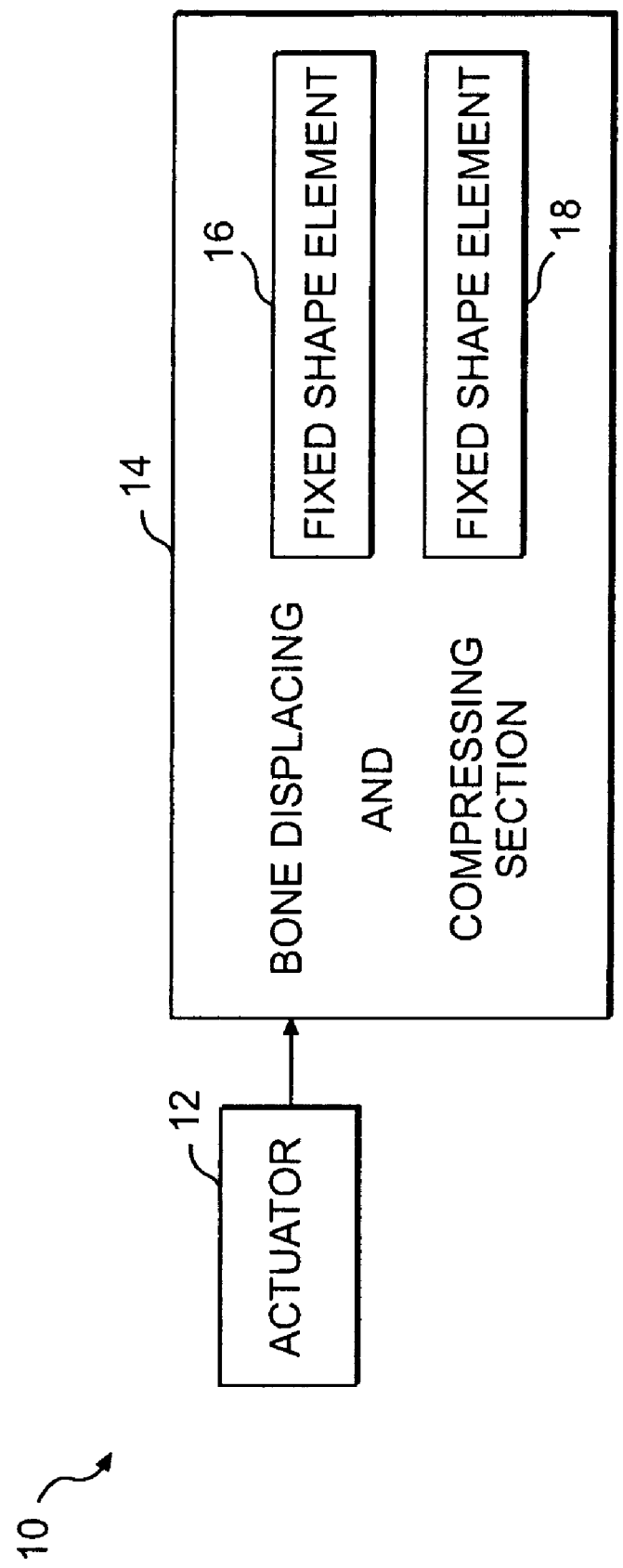
FIG. 1 is a schematic block diagram of an embodiment of the apparatus.
Figure 2A:
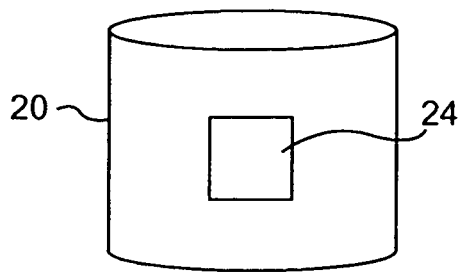
FIG. 2(a) is a schematic front view of a vertebra to which the intravertebral apparatus is applied and FIGS. 2(b), 2(c), 2(d), 2(e), 2(f)(1), and 2(f)(2) are schematic side views showing an intravertebral embodiment of the apparatus and a vertebra to which it is applied.
Figure 2B:
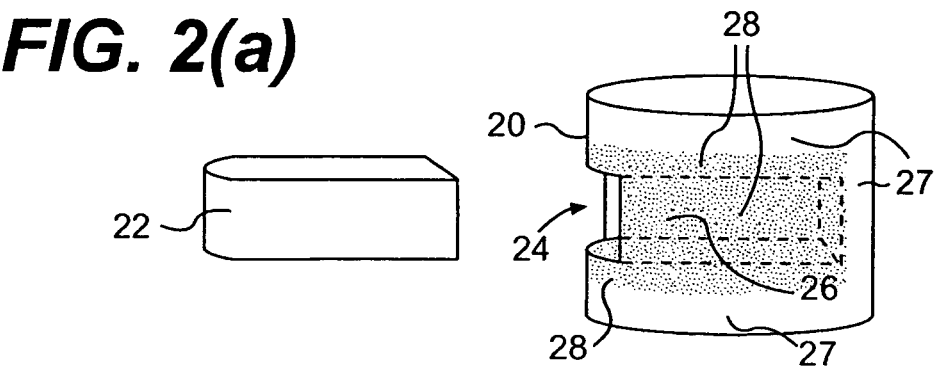
Figure 2C:
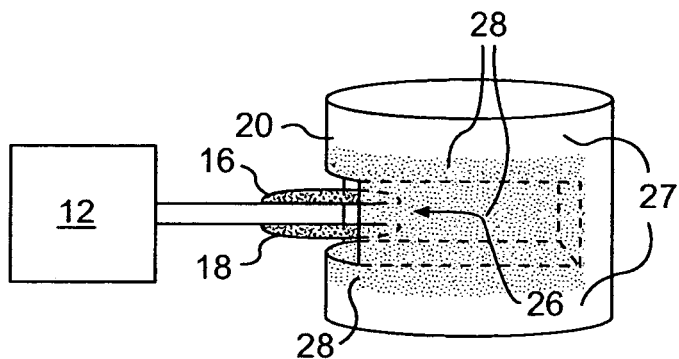
Figure 2D:
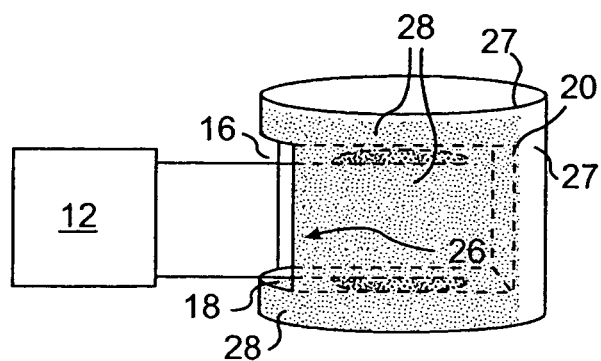

FIG. 1 shows an instrument 10 for contacting, displacing, compressing, and/or aligning two spaced apart portions of bone. The bone may be cancellous bone, cortical bone, or other types of bone. The degree of compression is selected to be sufficient to substantially strengthen the bone to substantially improve any subsequent repair thereto. The degree of displacement and the shape of the portion of the instrument contacting the bone are selected to create a specific and final desirable bone geometry. In the event that a medical fusion device, an artificial disc, a non-fusible spacer, or other medical device is to be subsequently positioned between the two spaced apart portions of bone, the instrument 10 reshapes and/or manipulates the bone to create a specific and desirable bone geometry that matches or accommodates the subsequently inserted device. In the event that autograft bone, allograft bone, synthetic bone, a bone graft substitute, and/or a biocompatible material is to be added to the compressed bone, the instrument 10 reshapes and/or manipulates the bone to accommodate the subsequently added material.

In one embodiment, the instrument 10 is an intravertebral tool, sized and configured to be inserted into a cavity formed within a single vertebra, to shape and enlarge the cavity, and to manipulate opposing portions of bone within the cavity. In another embodiment, instrument 10 is an intervertebral tool, sized and configured to be inserted between two adjacent vertebrae, to manipulate the bone of each vertebra, and to create a recess within each vertebra bounded by the bone. But it should be understood that the instrument 10 is also usable on structures other than spinal vertebrae. Additionally, although the instrument 10 is illustrated and described in the context of the treatment of a human spine, it should be understood that the instrument 10 may be used to treat other animals.

The instrument 10 comprises an actuator 12 and a bone displacing and compressing section 14. In an intravertebral embodiment, the bone displacing and compressing section 14 is sized and configured to be inserted through an opening in a cavity formed in a vertebral body. The bone displacing and compressing section 14 may act as a mechanical tamp, enlarging and shaping the cavity into which it is inserted by displacing bone that it encounters. In an intervertebral embodiment, the displacing and compressing section 14 is sized and configured to be inserted between two adjacent vertebrae. In both embodiments, the actuator 12 actuates the bone displacing and compressing section 14 so that the section 14 may move within a space in which the section 14 is inserted (within or between bones), so that the section 14 may contact and displace bone encountered by the section 14, and so that the section 14 may compress and strengthen the bone it contacts after insertion. Embodiments may differ in the length of time the section 14 is actuated by the actuator 12 to displace and/or compress or manipulate the bone, the amount of force the section 14 applies to the bone, and the speed with which the section 14 is actuated to move within a vertebral body or between vertebrae. In the intravertebral embodiment, the actuator 12 actuates the section 14 to apply less force to the bone, for less time, and to move at a slower speed than in the intervertebral embodiment.

Figure 3:
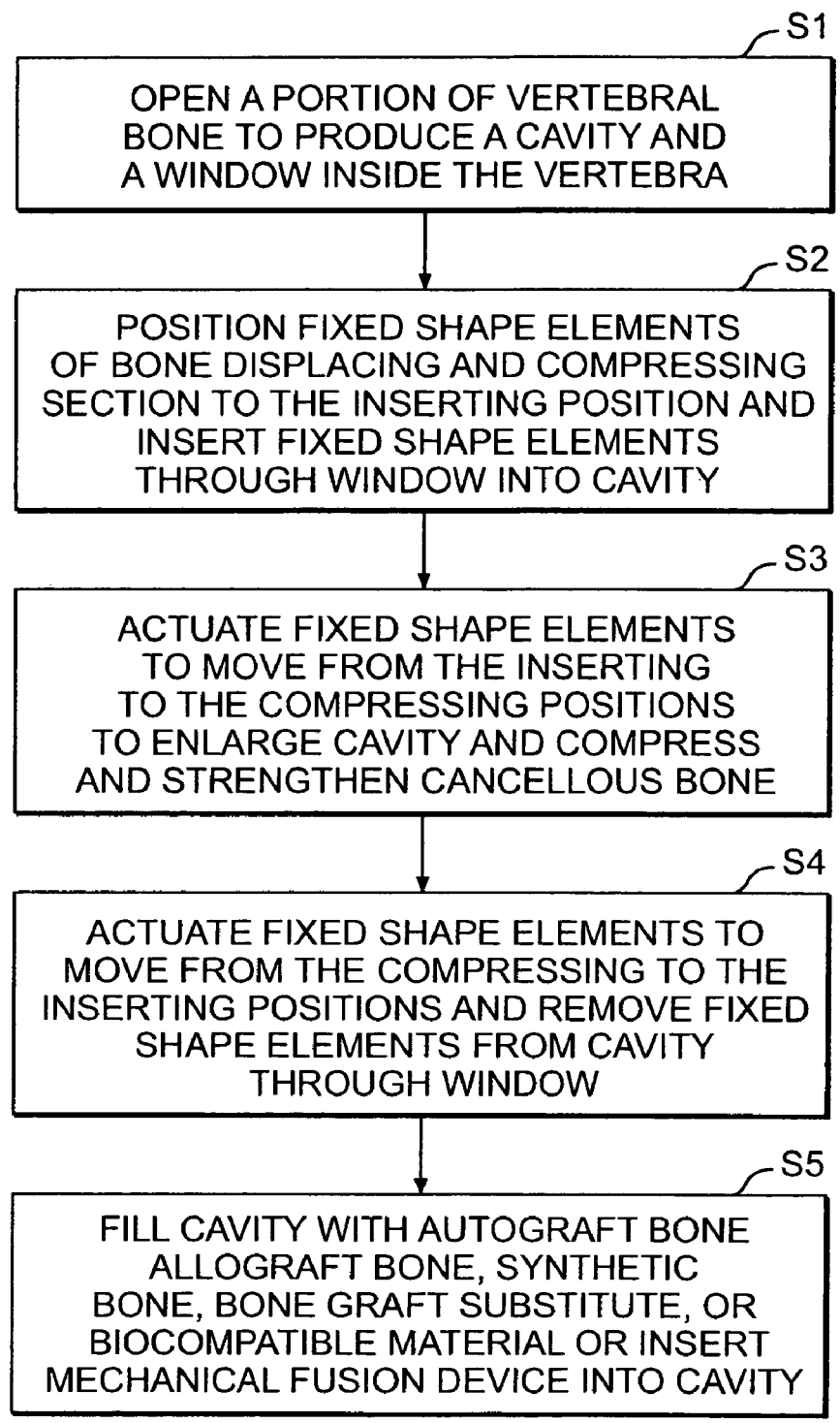
FIG. 3 shows a flow chart of an intravertebral method.

In one embodiment, the instrument 10 is inserted into the space between the two spaced apart portions of bone, the actuator 12 actuates the section 14 to perform one displacing and compression operation on the two spaced apart portions of bone, the instrument 10 is removed, and the bone is repaired, further strengthened, and/or reshaped, by for example, adding allograft bone, autograft bone, synthetic bone, bone graft substitute, or biocompatible material to the compressed bone, as shown in FIGS. 3 and 5 and as will be discussed in more detail below. In another embodiment, after the bone-compressing and material-adding steps, the instrument 10 is again inserted into the space between the two spaced apart portions of bone, and the actuator 12 actuates the section 14 to perform another displacing and compressing operation. This time, though, the bone is compressed through contact between the section 14 and the added material. Then, the instrument 10 is removed. This alternative embodiment is shown in FIG. 6, which will be discussed in more detail below. Moreover, this process of compressing and adding material to the bone can be repeated until the bone is rebuilt to possess a desired geometry.

The actuator 12 can comprise any type of device known to those skilled in the art for actuating the section 14 to move, and to displace and compress bone, such as a mechanical actuator, a pneumatic actuator, an electrical actuator, an electromechanical actuator, or a hydraulic actuator. Two examples of a mechanical actuator are shown in FIGS. 7, 8(a), and 8(b), which will be discussed below.

The bone displacing and compressing section 14 may comprise two fixed shape elements 16 and 18 that are actuated to move by the actuator 12 in opposite directions along a single axis to produce a continuous compressing force applied to vertebral bone. But it is within the scope of the present invention for the actuator 12 to actuate the elements 16 and 18 to perform controlled directional displacement in directions other than opposite directions with respect to each other. For example, it is within the scope of the present invention for the elements 16 and 18 to move in directions at a 45 degree or a 90 degree angle with respect to each other, or at any other angle between 0 and 180 degrees. It is also within the scope of the present invention for the section 14 to comprise a single, fixed shape, bone displacing and compressing element or more than two fixed shape, bone displacing and compressing elements.

The shape of the elements 16 and 18 is selected so as to produce a substantially stable vertebra as a result of reshaping, manipulating, compressing, and/or strengthening the vertebra with the elements 16 and 18, and a) subsequently bonding allograft bone, autograft bone, synthetic material, such as synthetic bone or bone graft substitute, or biocompatible material to the vertebra, or b) subsequently bonding or attaching an attachment mechanism to the vertebra. More specifically, the fixed shape elements 16 and 18 may be hemispherically shaped, or spoon shaped, or have a flat outer peripheral surface. In addition, the shape of the elements 16 and 18 can be selected to accommodate or match the shape of the subsequent graft or a subsequently inserted artificial disc or medical device. It is also within the scope of the present invention for these elements to be in the shape of: a convex polyhedron, such as a cube, a dodecahedron, a icosahedron, an octahedron, and a tetrahedron; an Archimedean solid; a Catalan solid; a uniform polyhedron; an irregular solid; a sphere; an ellipsoid; an ovoid; a rectangular solid; a cylinder; or a cone. It is further within the scope of the present invention for the elements 16 and 18 to be in the shape of: a part of a convex polyhedron, such as a cube, a dodecahedron, a icosahedron, an octahedron, and a tetrahedron; a part of an Archimedean solid; a part of a Catalan solid; a part of a uniform polyhedron; a part of an irregular solid; a part of a sphere; a part of an ellipsoid; a part of an ovoid; a part of a rectangular solid; a part of a cylinder; or a part of a cone.

The elements 16 and 18 may have the same shape or may be shaped differently from each other. In addition, the elements 16 and 18 may be detachable from the section 14 so that differently shaped elements 16 and 18 may be attached to the section 14. This detachable embodiment is useful when performing repeated compression and filling operations that require the elements 16 and 18 to have a different shape during different compression operations. When the shape of the element 16 and/or the element 18 is to be changed after the first compression operation, the element 16 and/or the element 18 may be simply detached from the section 14 and replaced with an element or elements of a different shape. Alternatively, different instruments 10 having differently shaped elements 16 and 18 may be used during different compression operations.

The fixed shape elements 16 and 18 are movable by the actuator 12 from an inserting position to a compressing position. In the inserting position, the elements 16 and 18 are closer together than in the compressing position. In one embodiment, in the inserting position, the elements 16 and 18 are adjacent or make contact with each other, and in another embodiment, they are merely closer to each other than in the compressing position. In the compressing position, the fixed shape elements 16 and 18 are spaced apart by the distance needed to contact the bone within a single vertebra or between vertebrae to compress the bone with a sufficient force for a sufficient amount of time to strengthen the bone for one of the repair protocols noted below.

In one embodiment, the elements 16 and 18 are moved only once substantially along a single axis in opposite directions from the inserting position to the compressing position to compress and strengthen the vertebral bone in a single continuous compressing operation. In another embodiment, the two elements 16 and 18 are moved multiple times substantially along the single axis in opposite directions from the inserting position to the compressing position to compress and strengthen the vertebral bone in multiple continuous compressing operations with the addition of bone-repair materials between the compressing operations. The two elements 16 and 18 may substantially simultaneously displace and compress the vertebral bone or the elements 16 and 18 may displace and compress the vertebral bone at completely different times, or at overlapping times, i.e., before one of elements 16 and 18 is finished displacing and compressing bone, the other of elements 16 and 18 starts displacing and compressing bone.

Intravertebral Tool and Method

In the intravertebral embodiment, the size and configuration of the elements 16 and 18 are selected so that the elements 16 and 18: 1) can be inserted in the inserting position through an opening in the cavity of a single vertebral body; and 2) can be moved apart by the actuator 12 from the inserting position to the compressing position to compress the bone by the amount needed to strengthen the bone for one of the repair protocols noted below. Movement of the elements 16 and 18 from the inserting to the compressing position may also enlarge the cavity and/or reshape the cavity into a desired shape to accommodate any material or device subsequently inserted into the cavity, for example, for repair and/or strengthening purposes.

This procedure, sometimes called a window osteotomy with compaction, is shown in FIGS. 2(*a*), 2(*b*), 2(*c*), 2(*d*), 2(*e*), 2(*f*)(1), and 2(*f*)(2). FIG. 3 illustrates the method steps accompanying the physical manipulation of the intravertebral tool 10 and a portion of a vertebra 20 shown in FIGS. 2(*a*) through 2(*f*)(2). FIGS. 2(*a*) through 2(*f*)(2) do not show the other tissue or bones surrounding the vertebra 20, and it is assumed that prior to the step shown in FIG. 2(*a*), the surgeon has created a clear path between the instrument 10 and the vertebra 20 via any surgical procedure known to those skilled in the art if such a clear path does not exist prior to surgery.

FIG. 2(*a*) and FIG. 2(*b*) show front and side views of a portion of the vertebra 20 that has suffered some damage or in which pathology exists, such as a compression fracture (not shown), or needs to be strengthened. In step S1, a surgeon cuts out or drills out a portion 22 of the vertebral cortical bone, for example with a box chisel, to produce a window 24 into the interior of the vertebra 20, as shown in FIGS. 2(*a*) and 2(*b*), and to create a cavity 26 in the vertebra, as shown in FIG. 2(*b*). The window 24 can be cut at such a position in the vertebra 20 so as to permit anterior, posterior, lateral, or anteriolateral access into the interior thereof. The interior of the vertebra 20 contains cortical bone 27 and cancellous bone 28. The instrument 10 may be used to compress or reposition one or both of the cortical bone 27 and the cancellous bone 28. In step S2, the surgeon positions the elements 16 and 18 to the inserting position if they are not already in that position and inserts the elements 16 and 18 through the window 24 into the cavity 26, as shown in FIG. 2(*c*). This step may entail activating the actuator 12 to move the elements 16 and 18 to the inserting position, or in one embodiment, the surgeon may also move the elements 16 and 18 manually to the inserting position.

In step S3, the surgeon activates the actuator 12 to actuate the elements 16 and 18 to move from the inserting position to the compressing position, as shown in FIG. 2(*d*). In this step, the actuator 12 accelerates the elements 16 and 18 in opposite directions to contact, displace, and compress the bone at the top and the bottom of the cavity 26. In addition, or alternatively, the actuator 12 accelerates the elements 16 and 18 to realign bone fragments of the vertebra 20 in the anterior-posterior direction, the medial-lateral direction, or the superior-inferior direction. As a result of this single continuous compression operation along a single vertical axis, the cavity 26 is enlarged and the resulting bony structure is made more dense as it is compressed and is thereby strengthened. In step S4, the surgeon activates the actuator 12 to actuate the elements 16 and 18 to move from the compressing position to the inserting position and then removes the instrument 10 from the cavity 26 through the window 24, as shown in FIG. 2(*e*). In step S5, the surgeon fills the cavity 26 with allograft bone, autograft bone, biocompatible material, bone graft substitute, or synthetic material, such as PMMA (polymethylmethacrylate), collectively denoted by reference characters 29*a*, as shown in FIG. 2(*f*)(1), or inserts an implant or medical device 29*b* into the cavity to further strengthen the vertebra, as shown in FIG. 2(*f*)(2). When an implant is used as the element 29*b*, the implant can be composed of any suitable material to repair the bone, as known to those skilled in the art, such as titanium, stainless steel, or a polymer, such as PEEK (polyetheretherketone). Alternatively, a medical device 29*b* that does not fuse to the bone of the vertebra 20 can be inserted into the cavity 26 to repair the vertebra 20. Thus, the instrument 10 strengthens the bone prior to repair, rebuilding, and/or remodeling.

It is within the scope of the present invention to perform steps S2 through S5 on a vertebra previously filled with autograft bone, allograft bone, bone graft substitute, biocompatible material, or synthetic material, such as PMMA, or into which an implant or a medical device was previously inserted. In this case, the material, the implant, or the medical device that was inserted into the cavity 26 is removed before steps S2 through S5 are performed. It is also within the scope of the present invention to perform steps S2 through S5 again, after the bone has been compressed once and the cavity 26 has been newly filled with autograft bone, allograft bone, bone graft substitute, biocompatible material, or synthetic material, or after the insertion of an implant or a medical device into the cavity. In this case, the elements 16 and 18 contact and displace the autograft bone, the allograft bone, the bone graft substitute, the biocompatible material, the synthetic material, the implant, or the medical device, and compress the vertebral bone through the autograft bone, the allograft bone, the bone graft substitute, the biocompatible material, the synthetic material, the implant, or the medical device. Additional autograft bone, allograft bone, bone graft substitute, biocompatible material, or synthetic material may then be inserted into the cavity 26. This repeated cavity-filling and tamping step may be performed multiple times.

It is also within the scope of the present invention to position the first and second elements 16 and 18 so that the distance between the outer periphery of these two elements is smaller than or precisely matches the width of the window 24 prior to insertion. As a result, as the elements 16 and 18 are inserted into the cavity 26, they slide on and contact the top and bottom portions of bone. After insertion, in this embodiment, the actuator 12 actuates the elements 16 and 18 to compress the bone from this position of contact.

In the event that the cavity 26 is to be filled with autograft bone, allograft bone, bone graft substitute, biocompatible material, or synthetic material, the actuator 12 actuates the first and second elements 16 and 18 to compress the two spaced apart portions of vertebral bone with sufficient force and for a sufficient amount of time to substantially strengthen the vertebral bone prior to subsequently filling the cavity 26 with the autograft bone, the allograft bone, the bone graft substitute, the biocompatible material, or the synthetic material. In addition, the actuator 12 actuates the first and second elements 16 and 18 to compress the two spaced apart portions of vertebral bone with sufficient force and for a sufficient amount of time to strengthen the vertebral bone subsequently filled with the autograft bone, the allograft bone, the bone graft substitute, the biocompatible material, or the synthetic material substantially above the strength the vertebra 20 would possess if the vertebra 20 were filled with autograft bone, the allograft bone, the bone graft substitute, the biocompatible material, or the synthetic material without being previously compressed by the elements 16 and 18.

In the event that the cavity 26 is to be filled with autograft bone, allograft bone, bone graft substitute, biocompatible material, or synthetic material and a pedicle screw is to be fixed to the vertebra 20, the actuator 12 actuates the first and second elements to compress the two spaced apart portions of vertebral bone with sufficient force and for a sufficient amount of time to substantially augment subsequent pedicle screw fixation on the vertebra 20.

In the event that an implant is to be inserted into the cavity 26 to subsequently fuse to the two spaced apart portions of bone, the actuator 12 actuates the first and second elements 16 and 18 to compress the two spaced apart portions of vertebral bone with sufficient force and for a sufficient amount of time to increase the strength of the vertebra 20 subsequently fused to the implant substantially above the strength the vertebra 20 would possess if the implant-fused vertebra 20 was not previously compressed by the first and second elements 16 and 18.

In the event that the vertebra 20 has a compression fracture and the cavity 26 is to be filled with autograft bone, allograft bone, bone graft substitute, biocompatible material, or synthetic material, the actuator 12 actuates the first and second elements 16 and 18 to compress the two spaced apart portions of vertebral bone with sufficient force and for a sufficient amount of time to substantially strengthen the vertebral bone prior to filling the cavity with the autograft bone, the allograft bone, the bone graft substitute, the biocompatible material, or the synthetic material. In addition, in this case, the actuator 12 actuates the first and second elements 16 and 18 to compress the two spaced apart portions of vertebral bone with sufficient force and for a sufficient amount of time to substantially restore the anatomical structure of the vertebra 20 after the cavity is filled with the autograft bone, the allograft bone, the bone graft substitute, the biocompatible material, or the synthetic material. Further in this case, the actuator 12 actuates the first and second elements 16 and 18 to compress the two spaced apart portions of vertebral bone with sufficient force and for a sufficient amount of time to increase the strength of the vertebra 20 after fusing to the autograft bone, the allograft bone, the bone graft substitute, the biocompatible material, or the synthetic material substantially above the strength the vertebra 20 would possess if the vertebra 20 was subsequently filled with the autograft bone, the allograft bone, the bone graft substitute, the biocompatible material, or the synthetic material without being previously compressed with the first and second elements 16 and 18.

Intervertebral Embodiment

In the intervertebral embodiment, the size and configuration of the elements 16 and 18 are selected so that the elements 16 and 18 can be inserted into the space between two adjacent vertebrae 30 when the elements 16 and 18 are in the inserting position. In addition, the moving of the elements 16 and 18 from the inserting to the compressing position by the actuator 12 can compress portions of each vertebra and create a recess in each vertebra bordered by the compressed bone of that vertebra. Further, the actuator 12 may actuate the elements 16 and 18 to compress the vertebral bone sufficiently 1) to strengthen the vertebral bone, 2) to substantially improve the functioning of any structure comprising the strengthened vertebrae and an intervertebral disc (not shown) or element positioned therebetween, such as a fusion device, a non-fusible device, or a disc-arthroplasty device, 3) to substantially improve the results of a revision repair, such as a disc-cage repair, a bone-nucleus repair, or a revision disc arthroplasty, which repairs a previously-repaired vertebral structure requiring further repair, and/or 4) to strengthen a structure comprising the compressed bone and a material or an element subsequently fused thereto substantially above the strength of such a structure formed without compression by elements 16 and 18.

This procedure is called endplate access with impaction grafting because access to the vertebrae is gained through the area where the endplates of an intervertebral disc attach to the vertebrae, as shown in FIGS. 4(a), 4(b), 4(c), 4(d), 4(e), 4(f), and 4(g). FIG. 5 shows the method steps accompanying the physical manipulation of the intervertebral tool and the vertebrae 30 shown in FIGS. 4(a) through 4(g). FIGS. 4(a) through 4(g) do not show the other tissue or bones surrounding the vertebrae 30. Moreover, prior to the steps shown in FIGS. 4(a) through 4(g), the surgeon can create access to the vertebrae 30 by removing the intervertebral disc and/or portions of their endplates (not shown). This operation permits access to the vertebrae 30 through the areas in which the endplates were attached, so that a clear path exists between the instrument 10 and the vertebrae 30.

Alternatively, the surgeon can remove the intervertebral disc while leaving the endplates attached to the vertebrae 30. In this alternative embodiment, the elements 16 and 18 directly contact the endplates and compress the bone of the vertebrae 30 through their contact with the endplates. Moreover, since the endplates may also contain cancellous bone, the compressing operation of the elements 16 and 18 also compresses and strengthens any cancellous bone existing in and below the endplates. In addition, since the endplates may contain osteoporotic, diseased, or damaged cortical bone, the elements 16 and 18 may also compress such bone when moving from the inserting to the compressing position. While this end-plate compression and strengthening is not shown in FIGS. 4(a) through 4(g) or FIG. 5, it is within the scope of the present invention to practice each of the steps shown in FIGS. 4(a) through 4(g) and FIG. 5 on two endplates attached to the vertebrae 30 to compress and strengthen the bone of the endplates and of the vertebrae 30 in a single, continuous compression operation.

Figure 4A:
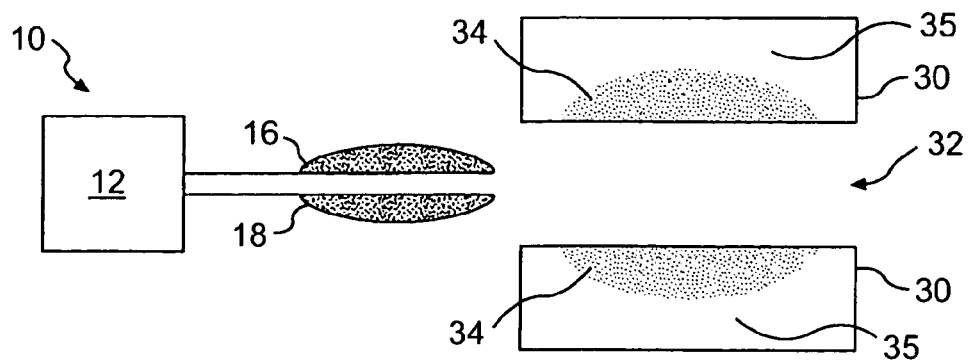
Figure 4B:
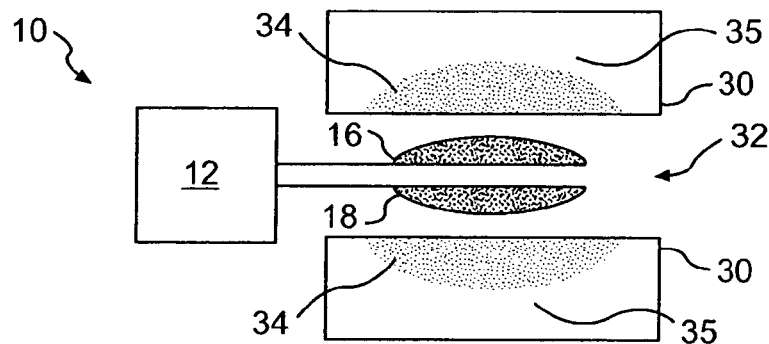
Figure 4C:
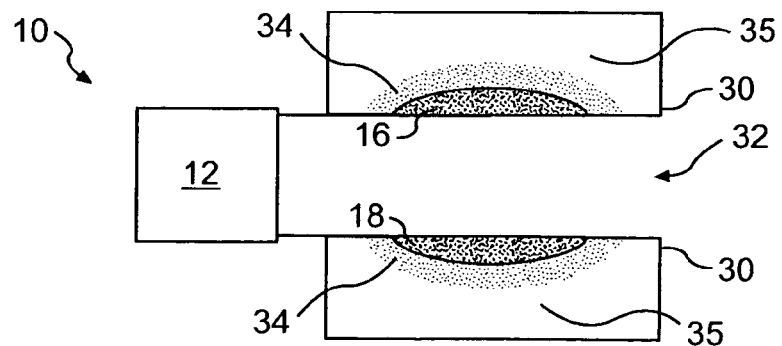

FIG. 4(a) shows a schematic side view of two spaced apart vertebrae 30, that have suffered damage, such as a compression fracture, or need to be strengthened. In FIG. 4(a), the instrument 10 is positioned a distance away from a space 32 between the vertebrae 30, either outside the body, or inside the body, but not yet inserted into the space 32 between the vertebrae 30. In step S10, the surgeon positions the elements 16 and 18 to the inserting position if they are not already in that position and inserts the elements 16 and 18 into the space 32 between the vertebrae 30, as shown in FIG. 4(b). This step may entail activating the actuator 12 to move the elements 16 and 18 to the inserting position, or in one embodiment, the surgeon may also move the elements 16 and 18 manually to the inserting position. The vertebrae 30 contains cancellous bone 34 and cortical bone 35. The instrument 10 may be used to compress one or both of the cancellous bone 34 and the cortical bone 35. In step S11, the surgeon activates the actuator 12 to actuate the elements 16 and 18 to move from the inserting position to the compressing position, as shown in FIG. 4(c). In this step, the actuator 12 accelerates the elements 16 and 18 in opposite directions to contact, displace, and compress the bone of the two vertebrae 30 at the top and the bottom of the space 32. As a result of this single continuous compression operation along a single vertical axis, a recess 36 is formed within each vertebra 30 bounded by the compressed bone, and the bone is compressed and strengthened.

Figure 4D:
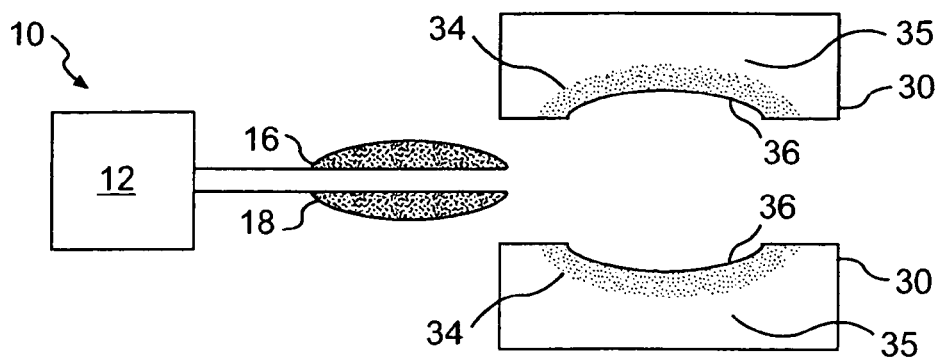
Figure 4G:
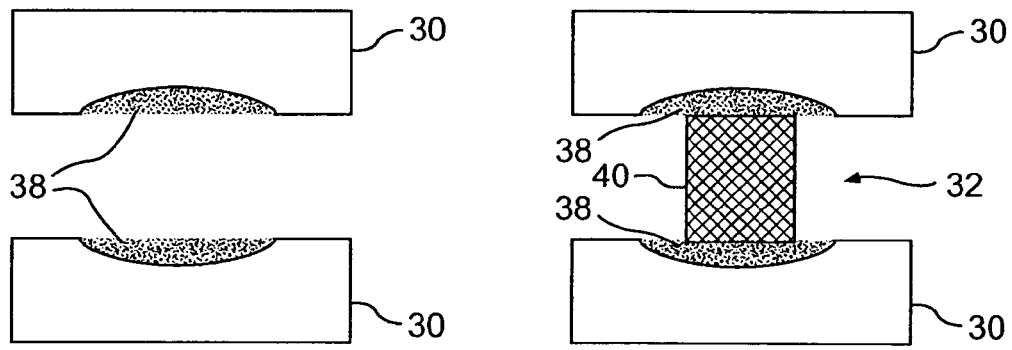
Figure 4G:
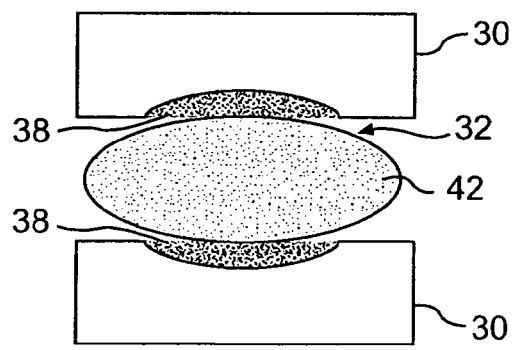

In step S12, the surgeon activates the actuator 12 to actuate the elements 16 and 18 to move from the compressing position to the inserting position and removes the instrument 10 from the space 32, as shown in FIG. 4(d). In step S13, the surgeon fills the recesses 36 of each vertebra 30 with allograft bone, autograft bone, bone graft substitute, biocompatible material, or synthetic material, collectively denoted by reference numeral 38, as shown in FIG. 4(e). This step S13 is optional. In the event that step S13 is not performed, in the embodiment in which an implant is subsequently inserted between the two vertebrae 30, the implant fuses directly to the compressed and strengthened bone of the two vertebrae 30. Returning to the embodiment shown in FIGS. 4(a) through 4(g), if a spinal fusion procedure is to be performed, the surgeon performs step S14 to insert an implant 40 into the space 32 to contact the allograft, autograft, bone graft substitute, biocompatible material, or synthetic material applied to the recesses 36, as shown in FIG. 4(f). If a primary disc arthroplasty procedure is to be performed, the surgeon performs step S15 to insert an artificial disc 42, as shown in FIG. 4(g).

It is also within the scope of the present invention to perform steps S10 through S12 as part of a revision disc arthroplasty, in which the vertebrae 30 were previously filled with autograft bone, allograft bone, bone graft substitute, biocompatible material, or synthetic material and an artificial disc was previously implanted between the vertebrae 30. In this case, the artificial disc and the allograft, autograft, bone graft substitute, biocompatible material, or synthetic material that were inserted into the recesses 36 are removed before steps S10 through S12 are performed.

In addition, it is within the scope of the present invention to perform steps S10 through S12 again, after the bone of the vertebrae 30 has been compressed once by the instrument 10 and the recesses 36 have been newly filled with autograft bone, allograft bone, bone graft substitute, biocompatible material, or synthetic material. As a result, the elements 16 and 18 compress the bone of the vertebrae 30 through contact with the autograft bone, the allograft bone, the bone graft substitute, the biocompatible material, or the synthetic material. It is also within the scope of the present invention to perform these repeated tamping and filling operations multiple times. Such an embodiment is shown in FIG. 6 and will now be further discussed.

Steps S20 through S23 are the same as steps S10 through S13 and are, therefore, not further discussed. After step S23, the surgeon again inserts the instrument 10 between the vertebrae 30, manipulates and compresses the bone of each vertebra 30 with the elements 16 and 18 to create another recess or reform the previously formed recess in each vertebra 30, removes the instrument 10, and again fills the recesses with autograft bone, allograft bone, bone graft substitute, biocompatible material, or synthetic material, in step S24. This repetition of steps S20 through step S23 can be performed one or more times to create a desired bone geometry. In addition, this repetition of steps S20 through S23 can be performed one or more times to create a desired bone geometry to accommodate a subsequently inserted mechanical fusion device, artificial disc, non-fusible spacer, or other non-fusible medical device. After step S24, the surgeon inserts into the intervertebral space a mechanical fusion device in step S25 or an artificial disc, a non-fusible spacer, or other non-fusible medical device in step S26.

It is within the scope of the present invention to position the first and second elements 16 and 18 so that the distance between the outer periphery of these two elements is smaller than or precisely matches the width of the space 32 between adjacent vertebrae 30 prior to insertion. As a result, as the elements 16 and 18 are inserted into the space 32, they slide on and contact the top and bottom portions of the bone of the two vertebrae 30. After insertion, in this embodiment, the actuator 12 actuates the elements 16 and 18 to compress the bone from this position of contact.

In the event that the recess 36 of each vertebra 30 is to be filled with autograft bone, allograft bone, bone graft substitute, biocompatible material, or synthetic material, the actuator 12 actuates the first and second elements 16 and 18 to compress the vertebral bone of the two spaced apart vertebrae 30 with sufficient force and for a sufficient amount of time to create the recesses 36 and to substantially increase the strength of the vertebrae prior to filling the recesses 36 with autograft bone, allograft bone, bone graft substitute, biocompatible material, or synthetic material. In addition, in this case, the actuator 12 actuates the first and second elements 16 and 18 to compress the vertebral bone of the two spaced apart vertebrae 30 with sufficient force and for a sufficient amount of time to strengthen the vertebrae 30 subsequently filled with autograft bone, allograft bone, bone graft substitute, biocompatible material, or synthetic material substantially above the strength the two vertebrae 30 would possess if the two vertebrae 30 were subsequently filled with autograft bone, allograft bone, bone graft substitute, biocompatible material, or synthetic material without being previously compressed by the fixed shape elements 16 and 18.

In the event that the recess 36 of each vertebra 30 is to be filled with autograft bone, allograft bone, bone graft substitute, biocompatible material, or synthetic material and a fusible implant 38 is to be placed into the space 32 to join the two adjacent vertebrae 30 by subsequently fusing to vertebral bone and/or the autograft bone, the allograft bone, the bone graft substitute, the biocompatible material, or the synthetic material in each recess 36, the actuator 12 actuates the first and second elements 16 and 18 to compress the vertebral bone of the two spaced apart vertebrae 30 with sufficient force and for a sufficient amount of time to substantially increase the strength of the vertebrae both before and after fusion to the fusible implant 40. This increased strength of the vertebrae 30 after fusion to the implant 40 is substantially greater than the strength the vertebrae 30 would possess if the vertebrae 30 were fused to the fusible implant 40 without being previously compressed by the elements 16 and 18.

In the event that a primary disc arthroplasty is to be performed so as to replace the intervertebral disc between the two adjacent vertebrae 30 with an artificial intervertebral disc 42, and in the event that the recess 36 of each vertebra 30 is to be filled with autograft bone, allograft bone, bone graft substitute, biocompatible material, or synthetic material, the actuator 12 actuates the first and second elements 16 and 18 to compress the vertebral bone of the two spaced apart vertebrae 30 with sufficient force and for a sufficient amount of time to substantially reinforce the subsequent primary disc arthroplasty substantially above the level of reinforcement that would exist if the two vertebrae 30 were not previously compressed by the first and second elements 16 and 18.

In the event that a revision disc arthroplasty is to be performed on a spinal structure defined by the two adjacent vertebrae 30 and an artificial intervertebral disc 42 positioned between the two adjacent vertebrae 30, and in the event that the recess 36 of each vertebra 30 is to be filled with autograft bone, allograft bone, bone graft substitute, biocompatible material, or synthetic material, the actuator 12 actuates the first and second elements 16 and 18 to compress the vertebral bone of the two spaced apart vertebrae 30 with sufficient force and for a sufficient amount of time to substantially reinforce the subsequent revision disc arthroplasty substantially above the level of reinforcement that would exist if the two vertebrae 30 were not previously compressed by the first and second elements 16 and 18.

Actuator Embodiments

FIG. 7 illustrates one mechanical embodiment of the actuator 12. The mechanical actuator 50 shown in FIG. 7 comprises a scissor-like device comprising first and second movable members 52 and 54 and a pivot element 56 around which members 52 and 54 rotate. The movable member 52 has a handle 58 at one end and the movable member 54 has a handle 60 at one end. The other end of the movable member 52 has attached thereto the fixed shape element 16, while the other end of the movable member 54 has attached thereto the fixed shape element 18. FIG. 7 shows the mechanical actuator 50 in the compressing position in which the fixed shape elements 16 and 18 and the handles 58 and 60 are spaced away from each other. When the surgeon grasps the handles 58 and 60 and moves them toward each other into an inserting position to minimize the distance therebetween, the fixed shape elements 16 and 18 also move toward each other to an inserting position. Conversely, when the surgeon moves the handles 58 and 60 in opposite directions away from each other into the compressing position, the fixed shape elements 16 and 18 move away from each other to the compressing position.

Although the elements 16 and 18 generally move in an arcuate path in response to movement of the handles 58 and 60, their movement from the inserting to the compressing position and from the compressing to the inserting position is substantially linear when moved over the distances required to act on two spaced apart portions of bone, as shown in FIG. 8(a). Alternatively, a different kind of mechanical actuator 12 can be provided that permits completely linear movement of the elements 16 and 18 over their entire range of motion. One example of such a device is the jack illustrated in FIG. 8(b). In this figure, the actuator 12 is in the form of a screw, one end of which is attached to a rotatable handle to be rotated by the surgeon, and the other end of which translates this rotary motion of the screw into rectilinear motion to move the elements of the displacing and compressing section 14 linearly. In both of these embodiments, the displacing and compressing section 14 is moved by the application of direct external power by hand. In the embodiment shown in FIG. 8(c), indirect external power is applied to the section 14 by a controller comprising the actuator 12. The controller controls the displacement of the section 14 by the use of an electromechanical mechanism, a hydraulic mechanism, or a pneumatic mechanism to move the section 14 and the elements 16 and 18 (not shown) linearly between the compressing and inserting positions. In addition, unlike the previous embodiments, the embodiments shown in FIGS. 8(b) and 8(c) each internally deploy a jack, which is part of the actuator for actuating movement of the elements 16 and 18, inside the space between the two spaced apart portions of vertebral bone.

Although several specific mechanical embodiments of the mechanical actuator 12 have been illustrated in FIGS. 7, 8(a), and 8(b), it should be understood that the use of other types and configurations of mechanical actuators are also contemplated, as would occur to one of ordinary skill in the art. More specifically, any type of mechanical actuator may be used that is capable of imparting relative displacement between the fixed shape elements 16 and 18 between the inserting and compressing positions.

In both the intervertebral and intravertebral embodiments, the amount of force used to manipulate or compress the bone and the amount of time during which this compression force is applied can be further determined by conducting various clinical tests, as are known to those skilled in the art.

While the present invention has been described with reference to the specific structures and embodiments disclosed herein, it is to be understood that it not limited to the details thereof, but is intended to cover such modifications or changes as may come within the scope of the following claims.

What is claimed is:

1. A method of strengthening two spaced apart portions of bone comprising:
   a) inserting an instrument having two fixed-shape, recess-producing elements into a space between the two spaced apart portions of the bone, the fixed-shape, recess-producing elements having fixed-shape, recess-forming surfaces shaped to compress bone to form a recess therein;
   b) producing a recess in the two spaced apart portions of bone and increasing the density of the two spaced apart portions of the bone by applying a sufficiently strong displacing and compressing force to produce a recess with each of the two fixed-shape, recess-producing elements to one of the two spaced apart portions of bone, to improve subsequent repair thereof;
   c) subsequently repairing the two spaced apart portions of the bone by performing one or both of: i) filling at least some of the space between the two spaced apart portions of the bone with autograft bone, allograft bone, bone graft substitute, biocompatible material, or synthetic material, and ii) inserting an element between the two spaced apart portions of the bone; and
   d) strengthening the two spaced apart portions of the bone in the recess-producing step by applying a sufficient force for a sufficient amount of time with the two fixed-shape, recess-producing elements to strengthen the two spaced apart portions of the bone sufficiently so that after the repairing operation, the strength of the two spaced apart portions of the bone is above the strength the two spaced apart portions of the bone would possess after the repairing operation if the two fixed-shape, recess-producing elements did not apply the displacing and compressing force to the two spaced apart portions of the bone.

2. The method defined by claim 1, wherein the two spaced apart portions of bone are positioned opposite from each other, and
   wherein the displacing and compressing forces applied by the two fixed shape elements are applied in opposite directions simultaneously to the two spaced apart portions of bone.

3. The method defined by claim 1, wherein the displacing and compressing force applied by each fixed shape element is applied only once.

4. The method defined by claim 1, wherein the displacing and compressing force applied by each fixed shape element is applied along only a single axis.

5. The method defined by claim 1, wherein the displacing and compressing force applied by each fixed shape element is applied only once along only a single axis in a single continuous compressing operation.

6. The method defined by claim 1, further comprising:
moving the two fixed shape elements toward each other into an inserting position before inserting the instrument into the space by moving two handles, each attached to one of the two fixed shape elements, toward each other; and
moving the two fixed shape elements away from each other into a displacing and compressing position by moving the two handles away from each other, so that the two fixed shape elements simultaneously contact, displace, and compress the two spaced apart portions of bone.

7. The method defined by claim 1, wherein the displacing and compressing force is applied to each of the two spaced apart portions of bone by applying a mechanical, a pneumatic, an electrical, or a hydraulic force to each of the two fixed shape elements to compress the two spaced apart portions of bone.

8. The method defined by claim 1, wherein the two spaced apart portions of bone comprise two spaced apart portions of vertebral bone positioned inside a cavity of a single vertebra, and wherein said method further comprises:
enlarging the cavity and compressing the vertebral bone with the two fixed shape elements.

9. The method defined by claim 8, wherein the two spaced apart portions of bone comprise two spaced apart portions of cancellous vertebral bone, and wherein the cavity is enlarged by displacing and compressing the cancellous vertebral bone with the two fixed shape elements.

10. The method defined by claim 8, further comprising:
displacing the two spaced apart portions of bone with the first and second elements to create a desired bone geometry, to accommodate the subsequent filling of the cavity with autograft bone, allograft bone, bone graft substitute, biocompatible material, or synthetic material, or to accommodate or match the shape of a subsequently inserted medical device or mechanical fusion device subsequently inserted into the cavity.

11. The method defined by claim 8,
wherein, in the event that the cavity is to be filled with autograft bone, allograft bone, bone graft substitute, biocompatible material, or synthetic material, the two fixed shape elements compress the two spaced apart portions of vertebral bone with sufficient force and for a sufficient amount of time to strengthen the single vertebra subsequently filled with the autograft bone, the allograft bone, the bone graft substitute, the biocompatible material, or the synthetic material above the strength the filled single vertebra would possess if the single vertebra was not compressed by the fixed shape elements,
wherein, in the event that the cavity is to be filled with autograft bone, allograft bone, bone graft substitute, biocompatible material, or synthetic material and a pedicle screw is to be fixed to the single vertebra, the two fixed shape elements compress the two spaced apart portions of vertebral bone with sufficient force and for a sufficient amount of time to augment the subsequent pedicle screw fixation on the single vertebra,
wherein, in the event that an implant is to be inserted into the cavity to fuse to the two spaced apart portions of bone, the two fixed shape elements compress the two spaced apart portions of vertebral bone with sufficient force and for a sufficient amount of time to strengthen the two spaced apart portions of the vertebral bone subsequently fused to the implant above the strength the single vertebra would possess if the implant-fused single vertebra was not previously compressed by the two fixed shape elements, or
wherein, in the event the single vertebra has a compression fracture and the cavity is to be filled with autograft bone, allograft bone, bone graft substitute, biocompatible material, or synthetic material, the two fixed shape elements compress the two spaced apart portions of vertebral bone with sufficient force and for a sufficient amount of time to restore the anatomical structure of the single vertebra when the single vertebra is filled with the autograft bone, the allograft bone, the bone graft substitute, the biocompatible material, or the synthetic material.

12. The method defined by claim 8, further comprising:
filling the cavity with autograft bone, allograft bone, bone graft substitute, biocompatible material, or synthetic material;
inserting the instrument into the space between the two spaced apart portions of the bone filled with autograft bone, allograft bone, bone graft substitute, biocompatible material, or synthetic material; and
applying a displacing and compressing force with each of the two fixed shape elements to the autograft bone, the allograft bone, the bone graft substitute, the biocompatible material, or the synthetic material with sufficient force and for a sufficient amount of time to strengthen the two spaced apart portions of bone.

13. The method defined by claim 1, wherein the two spaced apart portions of bone comprise two spaced apart portions of vertebral bone that are each part of one of two adjacent vertebrae, and
wherein the vertebral bone of the two adjacent vertebrae are compressed with sufficient force for a sufficient amount of time by the two fixed shape elements to create a recess bordered by compressed and strengthened bone within each vertebra.

14. The method defined by claim 13, wherein the two spaced apart portions of vertebral bone comprise two spaced apart portions of cancellous vertebral bone that are each part of one of two adjacent vertebrae, and
wherein the two fixed shape elements compress the cancellous vertebral bone of the two adjacent vertebrae with sufficient force for a sufficient amount of time to create a recess bordered by compressed and strengthened cancellous bone within each vertebra.

15. The method defined by claim 13, further comprising:
displacing the two spaced apart portions of vertebral bone with the first and second elements to create a desired bone geometry, to accommodate the subsequent filling of the recesses with autograft bone, allograft bone, bone graft substitute, biocompatible material, or synthetic material, or to accommodate or match the shape of a subsequently inserted medical device, mechanical fusion device, artificial disc, or non-fusible spacer inserted into the intervertebral space between the adjacent vertebrae.

16. The method defined by claim 13, further comprising:
filling the recesses with autograft bone, allograft bone, bone graft substitute, biocompatible material, or synthetic material;
inserting the instrument into the space between the two spaced apart portions of the vertebral bone whose recesses are filled with autograft bone, allograft bone, bone graft substitute, biocompatible material, or synthetic material; and
applying a displacing and compressing force with each of the two fixed shape elements to the autograft bone, the allograft bone, the bone graft substitute, the biocompatible material, or the synthetic material with sufficient force and for a sufficient amount of time to strengthen the two spaced apart portions of vertebral bone.

17. The method defined by claim 13, wherein, in the event that the recess of each vertebra is to be filled with autograft bone, allograft bone, bone graft substitute, biocompatible material, or synthetic material, the two fixed shape elements compress the bone of the two spaced apart vertebrae with sufficient force and for a sufficient amount of time to strengthen the two vertebrae subsequently fused to the autograft bone, the allograft bone, the bone graft substitute, the biocompatible material, or the synthetic material subsequently filling each recess, above the strength the two vertebrae would possess if the two vertebrae were subsequently fused to the autograft bone, the allograft bone, the bone graft substitute, the biocompatible material, or the synthetic material without being previously compressed by the two fixed shape elements, wherein, in the event that the recess of each vertebra is to be filled with autograft bone, allograft bone, bone graft substitute, biocompatible material, or synthetic material and an implant is to be placed into the space between the vertebrae to join the two vertebrae, the two fixed shape elements compress the vertebral bone of the two spaced apart vertebrae with sufficient force and for a sufficient amount of time to strengthen the two vertebrae subsequently fused to the implant above the strength the two vertebrae would possess if the two vertebrae were subsequently fused to the implant and the autograft bone, the allograft bone, the bone graft substitute, the biocompatible material, or the synthetic material without being previously compressed by the two fixed shape elements, wherein, in the event that a primary disc arthroplasty is to be performed so as to replace the intervertebral disc between the two adjacent vertebrae with an artificial intervertebral disc, and in the event that the recess of each vertebra is to be filled with autograft bone, allograft bone, bone graft substitute, biocompatible material, or synthetic material, the two fixed shape elements compress the vertebral bone of the two spaced apart vertebrae with sufficient force and for a sufficient amount of time to reinforce the subsequent primary disc arthroplasty, or wherein, in the event that a revision disc arthroplasty is to be performed on a spinal structure defined by the two adjacent vertebrae and an artificial intervertebral disc positioned between the two adjacent vertebrae, the two fixed shape elements compress the vertebral bone of the two spaced apart vertebrae with sufficient force and for a sufficient amount of time to reinforce the subsequent revision disc arthroplasty.

18. The method defined by claim 13, wherein an endplate of an intervertebral disc is positioned between each vertebra of the two adjacent vertebrae and one of the two fixed shape elements when the two fixed shape elements are inserted into the space between the two adjacent vertebrae, and the two fixed shape elements are applied against the two endplates, respectively, to displace each endplate against one of the adjacent vertebrae to compress bone of the two adjacent vertebrae with sufficient force for a sufficient amount of time to define the recess bordered by compressed and strengthened bone of each vertebra.

19. The method defined by claim 1, wherein said recess-producing and density-increasing step further comprises the step of strengthening the two spaced apart portions of bone.

20. The method defined by claim 1, wherein said recess-producing and density-increasing step produces a recess without cutting the two spaced apart portions of bone.

21. The method defined by claim 1, wherein said recess-producing and density-increasing step produces a recess in the two spaced apart portions of bone by applying only a displacing and compressing force with each of the two fixed-shape, recess-producing elements.

22. A method of strengthening two spaced apart portions of bone comprising:
a) inserting an instrument having two fixed-shape, recess-producing elements into a space between the two spaced apart portions of the bone, the fixed-shape, recess-producing elements having fixed-shape, recess-forming surfaces;
b) producing a recess in the two spaced apart portions of bone and increasing the density of the two spaced apart portions of the bone by applying a sufficiently strong displacing and compressing force to produce a recess with each of the two fixed-shape, recess-producing elements to one of the two spaced apart portions of bone;
c) filling in the recesses with autograft bone, allograft bone, synthetic bone, bone graft substitute or biocompatible material; and
d) strengthening the two spaced apart portions of the bone in the recess-producing step by applying a sufficient force for a sufficient amount of time with the two fixed-shape, recess-producing elements to strengthen the two spaced apart portions of the bone sufficiently so that after the filling operation, the strength of the two spaced apart portions of the bone is above the strength the two spaced apart portions of the bone would possess after the filling operation if the two fixed-shape, recess-producing elements did not apply the displacing and compressing force to the two spaced apart portions of the bone.

23. A method of manipulating two spaced apart portions in the interior of a bone comprising:
a) removing an outer part of the bone to produce a window into the interior of the bone with a first instrument to expose the two spaced apart portions in the interior of the bone;
b) inserting a second instrument having two fixed-shape, recess-producing elements through the window into a space in the interior of the bone between the two spaced apart portions, the fixed-shape, recess-producing elements having fixed-shape, recess-forming surfaces shaped to compress bone to form a recess therein;
c) producing a recess in the two spaced apart portions of bone and increasing the density of the two spaced apart portions in the interior of the bone by applying a sufficiently strong displacing and compressing force to produce a recess with each of the two fixed-shape, recess-producing elements to one of the two spaced apart portions;
d) subsequently repairing the bone by performing one or both of: i) filling at least some of the interior of the bone between the two spaced apart portions with autograft bone, allograft bone, bone graft substitute, biocompatible material, or synthetic material, and ii) inserting an element between the two spaced apart portions of the bone; and
e) strengthening the bone in the recess-producing step by applying a sufficient force for a sufficient amount of time with the two fixed-shape, recess-producing elements to strengthen the two spaced apart portions of the bone sufficiently so that after the repairing operation, the strength of the bone is above the strength the bone would possess after the repairing operation if the two fixed-shape, recess-producing elements did not apply the displacing and compressing force to the two spaced apart portions of the bone.

24. The method defined by claim 22, wherein the inserting step is performed during a surgical operation for improving bone function, and wherein the method further comprises placing the element into the space between the two spaced apart portions of the bone after the filling-in step and retaining the element in the space after the instrument is withdrawn from the space and the surgical operation is completed, wherein the element comprises one of a medical device, an implant, a mechanical fusion device, an artificial disc, and a non-fusible spacer.

* * * * *

UNITED STATES PATENT AND TRADEMARK OFFICE
CERTIFICATE OF CORRECTION

| | | |
|---|---|---|
| PATENT NO. | : 7,615,052 B2 | Page 1 of 1 |
| APPLICATION NO. | : 11/117301 | |
| DATED | : November 10, 2009 | |
| INVENTOR(S) | : Jon Serbousek | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 213 days.

Signed and Sealed this

Nineteenth Day of October, 2010

David J. Kappos
*Director of the United States Patent and Trademark Office*